United States Patent [19]

Usami et al.

[11] Patent Number: 4,875,981
[45] Date of Patent: Oct. 24, 1989

[54] OXYGEN ANALYZING METHOD AND DEVICE

[75] Inventors: Jun Usami, Aichi; Akinobu Hattori, Yokkaichi; Yuichi Sasaki, Nagoya, all of Japan

[73] Assignee: NGK Insulators, Ltd., Nagoya, Japan

[21] Appl. No.: 34,903

[22] Filed: Apr. 6, 1987

[30] Foreign Application Priority Data

Apr. 9, 1986 [JP] Japan .................. 61-81577

[51] Int. Cl.⁴ .................................. G01N 27/58
[52] U.S. Cl. ..................... 204/1 T; 204/406; 204/412; 204/425
[58] Field of Search .............. 204/410, 406, 412, 425, 204/1 S

[56] References Cited

U.S. PATENT DOCUMENTS

| | | | |
|---|---|---|---|
| 4,272,331 | 6/1981 | Hetrick | 204/1 T |
| 4,396,466 | 8/1983 | Hetrick et al. | 204/1 T |
| 4,578,171 | 3/1986 | Yamada et al. | 204/406 |
| 4,594,139 | 6/1986 | Asayama et al. | 204/410 |
| 4,601,809 | 7/1986 | Kitahara | 204/406 |
| 4,645,572 | 2/1987 | Nishizawa et al. | 204/1 T |
| 4,666,566 | 5/1987 | Mizutani et al. | 204/1 T |
| 4,707,241 | 11/1987 | Nakagawa et al. | 204/406 |
| 4,770,758 | 9/1988 | Suzuki et al. | 204/406 |
| 4,776,943 | 10/1988 | Kitahara | 204/427 |

*Primary Examiner*—G. L. Kaplan
*Attorney, Agent, or Firm*—Arnold, White & Durkee

[57] ABSTRACT

An oxygen analyzing method for determining a positive or negative oxygen concentration of a measurement gas which changes between oxidizing and reducing atmospheres. The method uses a sensing element having an oxygen sensing cell wherein an electromotive force is induced between its measuring and reference electrodes according to the principle of an oxygen concentration cell. The atmosphere adjacent to the measuring electrode is controlled by controlling a pumping current to be applied to an oxygen pumping cell such that the electromotive force induced in the sensing cell is maintained at a predetermined level. A heater is provided to heat the sensing and pumping cells, to maintain their operating temperature within a range of 700°–960° C. The pumping current, or a signal to control the pumping current, is converted into an oxygen concentration signal whose level is held within one of a positive range and a negative range. The concentration signal represents the positive oxygen concentration of the oxidizing atmosphere, or the negative oxygen concentration of the reducing atmosphere.

7 Claims, 4 Drawing Sheets

OXYGEN ANALYZING METHOD AND DEVICE

BACKGROUND OF THE INVENTION

1. Field of the Invention

The present invention relates in general to an oxygen analyzing method and a device suitable for practicing the method, and more particularly to a simple method and device for accurately determining positive and negative concentrations (for example, from $-10\%$ to $+20\%$) of oxygen in a measurement gas which changes at random between an oxidizing atmosphere and a reducing atmosphere, wherein the positive and negative oxygen concentrations are represented by a single output signal within either a positive range or a negative range.

2. Discussion of the Prior Art

Oxygen sensors utilizing an electrochemical reaction have been used in the field of controlling various industrial furnaces as used in steelworks, and various boilers. Such sensors employ a solid electrolyte such as zirconia exhibiting oxygen-ion conductivity at an elevated temperature, and are operated according to the principle of an oxygen concentration cell, to detect the oxygen concentration (oxygen partial pressure) of exhaust gases emitted by the furnaces or boilers, or atmospheres within the furances or boilers. The combustion or burning conditions of the furnaces or boilers can be monitored or controlled based on the detected oxygen concentration.

In a commonly used oxygen analyzing device for determining the oxygen concentration of such gases or atmospheres (measurement gases), an electrochemical oxygen sensing cell is constituted by a solid electrolyte body, and a pair of porous platinum electrodes disposed on the solid electrolyte body. One of the two electrodes is used as a reference electrode exposed to a reference gas such as an ambient air having a known oxygen partial pressure. The other electrode is used as a measuring electrode exposed to a measurement gas such as an exhaust gas, or an atmosphere within a furance. The oxygen partial pressure of the measurement gas is determined by detecting an electromotive force which is induced between the reference and measuring electrodes, based on a difference in oxygen partial pressure between the reference gas and the measurement gas. The electromotive force induced between the two electrodes is expressed by the well known Nernst equation, and the oxygen partial pressure of the measurement gas is readily calculated based on the the measured electromotive force, according to the Nernst equation.

The composition of the measurement gas such as exhaust gases or atmospheres within furances usually changes due to a variation in the air-fuel ratio (excess air ratio) of an air-fuel mixture. More specifically, the stoichiometric exhaust gas which is produced as a result of combustion of an air-fuel mixture having the stoichiometric air/fuel ratio (excess air ratio $\mu=1$), contains substantially no free oxygen. In the case where the exhaust gas is produced in combustion of an air-rich air-fuel mixture (whose excess air ratio is higher than 1), the exhaust gas is an oxidizing atmosphere which contains free oxygen in an amount corresponding to the amount of the excess air. On the other hand, if the exhaust gas is produced as a result of combustion of a fuel-rich air-fuel mixture (whose excess air ratio is lower than 1), the exhaust gas is a reducing atmosphere which does not contain free oxygen, but contains unburned components or incombustibles.

In the case where the measurement gas to be analyzed y an electromotive oxygen sensing cell changes at random between an oxidizing atmosphere and a reducing atmosphere, an electromotive force induced according to the principle of an oxygen concentration cell is varied as a function of the excess air ratio (air/fuel ratio). This relation between the induced electromotive force and the excess air ratio is known as a $\lambda$ curve (lambda curve), wherein the electromotive force suddenly changes in the neighborhood of the stoichiometric air/fuel ratio (excess air ratio $\mu=1$). Further, the pattern or slope of the curve of the oxidizing atmosphere is different from that of the reducing atmosphere. In the light of the above, the conventional oxygen sensor is adapted such that the oxygen concentration of the oxidizing atmosphere is obtained as an $O_2$ signal, while the negative oxygen concentration (amount of shortage of oxygen) of the reducing atmosphere is obtained as an $\alpha$ signal $[\alpha=(H_2+CO)/(H_2O+CO_2)]$. These two different output signals associated with the oxidizing and reducing atmospheres are independently produced by respective sensing elements incorporated in a single sensor body or two separate sensor bodies.

In the above arrangement, the ranges of the output signal level obtained by the two separate sensing elements for the oxidizing and reducing atmospheres are different, and therefore suitable adjustment or compensation is required to permit measurements of positive and negative oxygen concentrations on the same calibration basis. To this end, some calculating or control circuits or devices are necessary for such adjustment, and for selective processing of the two different output signals of the oxidizing and reducing atmospheres. Accordingly, the oxygen analyzing device as a whole tends to be complicated in construction.

Recently, there has been developed an oxygen sensing element which has an electrochemical sensing cell and an electrochemical pumping cell, for handling a measurement gas whose composition changes between an oxidizing and a reducing atmosphere. The pumping cell produces an electromotive force according to the principle of an oxygen concentration cell, between its measuring electrode exposed to the measurement gas, and its reference electrode exposed to a reference gas. The pumping cell is adapted to attain an oxygen pumping action for controlling the oxygen concentration of the atmosphere adjacent to the measuring electrode of the sensing cell, so that the electromotive force to be produced by the sensing cell is equal to a predetermined reference value. In this oxygen sensing element, the positive oxygen concentration of the oxidizing atmosphere, and the negative oxygen concentration (oxygen shortage amount) of the reducing atmosphere, are evaluated by detecting an amount of electric current (pumping current) that is applied to the pumping cell to achieve the intended oxygen pumping action.

According to the above arrangement having the oxygen sensing and pumping cells, however, the required pumping current (Ip) that is applied to the pumping cell while the measurement gas is a reducing atmosphere, is considerably varied depending upon the operating temperature of the sensing element. This variation means an undesirable measuring error due to a change in the sensor temperature. Described more specifically, even if the measurement gas is a reducing atmosphere obtained in combustion of an air-fuel mixture having a constant excess air ratio, namely, even if the reducing atmosphere has the same oxygen shortage amount (negative oxygen concentration), the well known water gas reaction of CO and $H_2$ is affected by the sensor temperature, and therefore the composition of the reducing atmosphere to be measured is varied with the sensor temperature. A difference in diffusion constant between CO and $H_2$ will cause a fluctuation in the pumping current (Ip) that is applied to the pumping cell.

SUMMARY OF THE INVENTION

It is accordingly an object of the present invention to provide an oxygen analyzing method for accurately determining positive and negative concentrations of oxygen in a measurement gas which changes between oxidizing and reducing atmospheres, wherein the positive and negative oxygen concentrations are obtained as a single output signal whose level is held within either a positive range or a negative range.

It is another object of the invention to provide a simple oxygen analyzing device suitable for practicing the above method of the invention.

According to one aspect of the present invention, there is provided an oxygen analyzing method for determining a positive or negative oxygen concentration of a measurement gas which changes at random between an oxidizing atmosphere and a reducing atmosphere, comprising the steps of: providing an electrochemical oxygen sensing cell wherein an electromotive force is induced according to the principle of an oxygen concentration cell, between a measuring electrode exposed to the measurement gas, and a reference electrode exposed to a reference gas; providing an electrochemical oxygen pumping cell adapted to effect an electrochemical oxygen pumping action for controlling an atmosphere adjacent to the measuring electrode of the sensing cell; providing a heater which cooperates with the sensing and pumping cells to form an integral laminar oxygen sensing element, and which is energized to heat the sensing and pumping cells; controlling the heater so as to maintain an operating temperature of the sensing and pumping cells within a range of 700°–960° C.; producing a pump control signal for controlling a pumping current to be applied to the pumping cell, to control the atmosphere adjacent to the measuring electrode so that the electromotive force induced between the measuring and reference electrodes is equal to a predetermined level; and converting the controlled pumping current or the produced current control signal, into an oxygen concentration signal whose level is held within one of a positive range and a negative range, the oxygen concentration signal representing the positive oxygen concentration of the measurement gas where the measurement gas is in a state of the oxidizing atmosphere, or the negative oxygen concentration of the measurement gas where the measurement gas is in a state of the reducing atmosphere.

In the oxygen analyzing method of the present invention described above, the level of the oxygen concentration signal produced by the above-described conversion is continuously varied within a positive range (for example, 0 V up to 1 V, or 4 mA up to 20 mA), or a negative range, which corresponds to a total range of variation of the positive and negative oxygen concentrations (for example, $-10\%$ to $+20\%$) of the measurement gas. In other words, the same oxygen concentration signal covers both the positive oxygen concentration range of the oxidizing atmosphere and the negative oxygen concentration range of the reducing atmosphere. Further, an error in the determination of the negative oxygen concentration due to fluctuation in the operating temperature of the sensing element is maintained at a considerably low level, since the operating temperature of the sensing element is maintained within the above-identified range. In this temperature range, the amount of pumping current that is controlled to achieve the intended pumping action is changed almost linearly as a function of the negative oxygen concentration, i.e., an additional amount of oxygen necessary to permit perfect combustion of a fuel-rich air-fuel mixture which results in the production of a reducing atmosphere. Thus, the instant oxygen analyzing method can be suitably practiced for accurate determination of the positive or negative oxygen concentration of an exhaust gas or atmosphere within a furnace or boiler, which changes from time to time between oxidizing and reducing atmospheres.

According to one feature of the instant method, a thermosensitive element is incorporated in the oxygen sensing element, for sensing the operating temperature of the sensing and pumping cells. In this case, the heater is controlled based on the operating temperature sensed by the thermosensitive element.

According to another feature of the instant method, the pumping current to be applied to the pumping cell is controlled so that the electromotive force induced in the sensing cell coincides with a level corresponding to a stoichiometric atmosphere whose oxygen concentration is zero. The stoichiometric atmosphere is produced in combustion of a stoichiometric air-fuel mixture whose excess air ratio is 1. Namely, the oxygen pumping action is controlled so that the oxygen concentration of the atmosphere adjacent to the measuring electrode is zeroed. In this arrangement, the level of the oxygen concentration signal represents the stoichiometric atmosphere, when the level of the pumping current or pump control signal is zero. The oxygen concentration signal whose level is lower than this stoichiometric level represents the negative oxygen concentration of the reducing atmosphere, while the same signal whose level is higher than the stoichiometric level represents the positive oxygen concentration of oxidizing atmosphere.

According to another aspect of the invention, there is provided an oxygen analyzing device for determining a positive or negative oxygen concentration of a measurement gas which changes at random between an oxidizing atmosphere and a reducing atmosphere, comprising: (1) an electrochemical oxygen sensing element including (a) an electrochemical oxygen sensing cell having a measuring electrode exposed to the measurement gas, and a reference electrode exposed to a reference gas, wherein an electromotive force is induced between the measuring and reference electrodes, according to the principle of an oxygen concentration cell, (b) an electrochemical oxygen pumping cell operable to effect an electrochemical oxygen pumping action for controlling an atmosphere adjacent to the measuring electrode of the sensing cell, (c) diffusion-resistance means through which the measurement gas diffuses toward the measuring electrode, under a predetermined diffusion resistance, and (d) a heater for heating the sensing and pumping cells; (2) a heater controller for controlling the heater so as to maintain an operating temperature of the sensing and pumping cells within a predetermined range; (3) a pumping-current controller which produces a pump control signal for controlling a pumping current to be applied to the pumping cell, to control the atmosphere adjacent to the measuring electrode so that the electromotive force induced between the measuring and reference electrodes is equal to a predetermined level; and (4) a converter for converting the controlled pumping current or the produced current control signal, into an oxygen concentration signal whose level is held within one of a positive range and a negative range, the oxygen concentration signal representing the positive oxygen concentration of the measurement gas where the measurement gas is in a state of the oxidizing atmosphere, or the negative oxygen concentration of the measurement gas where the measurement gas is in a state of the reducing atmosphere.

In accordance with one feature of the instant analyzing device, the oxygen sensing element further comprises a thermosensitive element integrally incorporated therein for sensing the operating temperature of the sensing and pumping cells, and a heater controller for controlling the heater, based on the operating temperature sensed by the thermosensitive element.

BRIEF DESCRIPTION OF THE DRAWINGS

The above and other objects, features and advantages of the present invention will be better understood by reading the following detailed description of preferred embodiments of the invention, when considered in connection with the accompanying drawings, in which.

DETAILED DESCRIPTION OF THE PREFERRED EMBODIMENTS

To further clarify the concept of the present invention, the preferred embodiments of the invention will be described in detail, by reference to the accompanying drawings.

Figure 1:
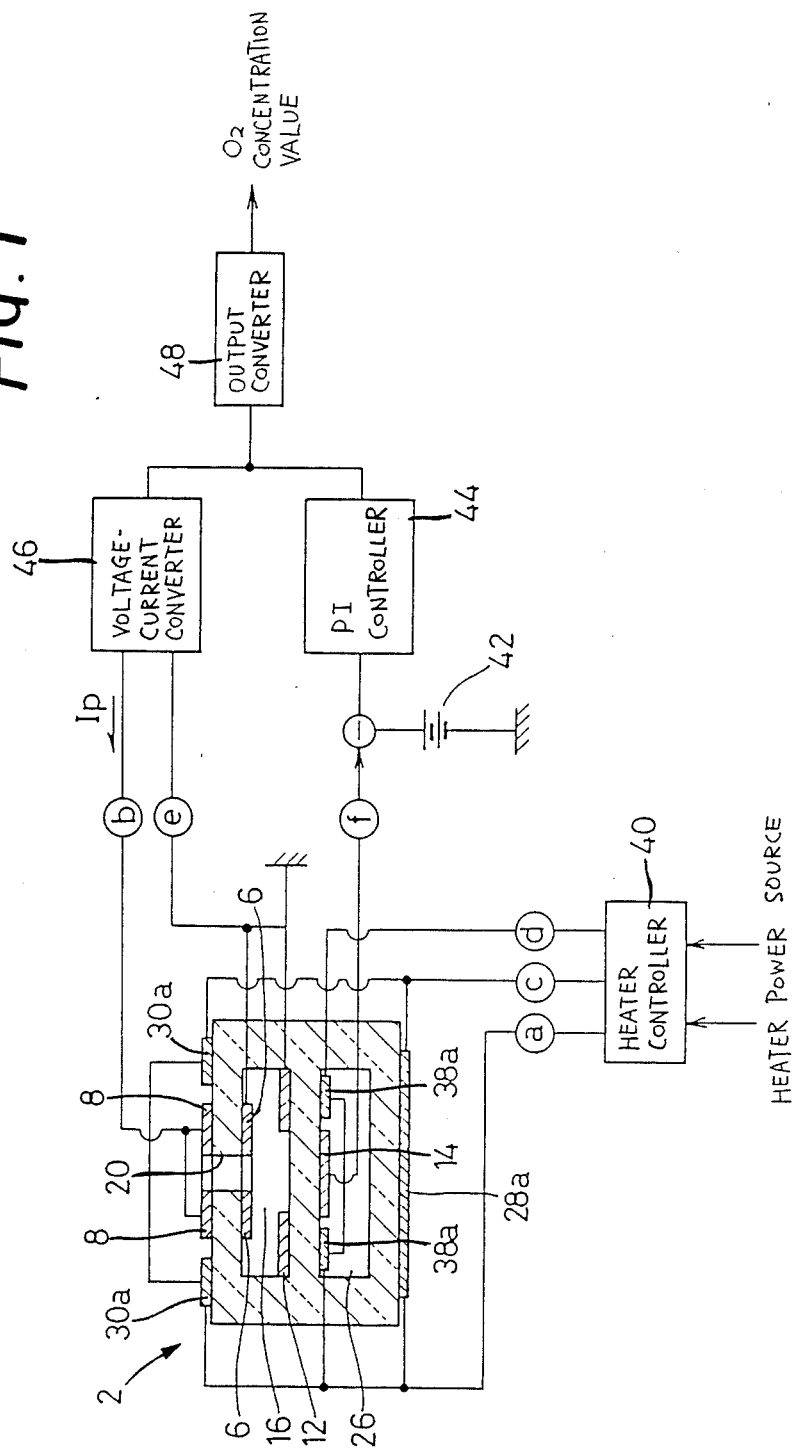
FIG. 1 is a schematic view illustrating one embodiment of an oxygen analyzing device of the present invention.

Referring first to FIG. 1, there is shown an oxygen analyzing device for determining positive and negative oxygen concentrations of a measurement gas according to the principle of this invention. The analyzing device includes an oxygen sensing element 2 which has a relatively narrow, generally elongate planar shape. The oxygen sensing element 2 has an oxygen detecting portion at its one longitudinal end, which is shown in transverse cross section in the figure. The detecting portion is adapted to operate according to the principle of an oxygen concentration cell, as well known in the art.

Figure 2:
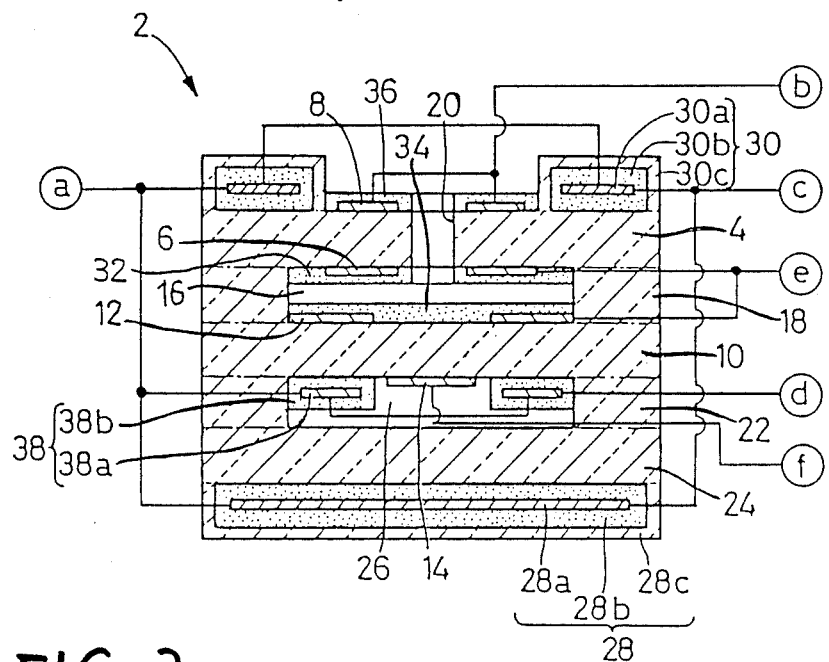
FIG. 2 is an elevational view in transverse cross section of an oxygen detecting end portion of one example of an oxygen sensing element used in the oxygen analyzing device of FIG. 1.

The oxygen detecting portion of this oxygen sensing element 2 has an integral laminar structure, as shown in detail in FIG. 2. More specifically, the laminar structure includes an electrochemical oxygen pumping cell and an electrochemical oxygen sensing cell which are formed on opposite sides of a diffusion chamber 16. The pumping cell consists of a first planar solid electrolyte body 4, and an inner and an outer porous pumping electrode 6, 8 which are formed on opposite major surfaces of the first planar solid electrolyte body 4. The solid electrolyte body 4 is made of stabilized oxygen-ion zirconia which exhibits oxygen-ion conductivity at an elevated temperature. Similarly, the sensing cell consists of a second planar solid electrolyte body 10, and a porous reference electrode 14 and a porous measuring electrode 12 which are formed on opposite major surfaces of the second planar solid electrolyte body 10. Between the oxygen pumping and sensing cells, there is disposed a spacer layer 18 which is made of a solid electrolyte and has a suitable thickness. This spacer layer 18 cooperates with the pumping and sensing cells to define the above-indicated diffusion chamber 16 in the form of a thin flat space which has a predetermined diffusion resistance to the molecules of a measurement gas. The oxygen pumping cell has a gas-inlet aperture 20 formed therethrough, such that the aperture 20 communicates at its one end with an external space in which the measurement gas exists, and at its other end with a central portion of the thin flat diffusion chamber 16. The measurement gas introduced through the gas-inlet aperture 20 diffuses into the diffusion chamber 16 under the predetermined diffusion resistance, so that the inner pumping electrode 6 of the pumping cell is exposed to the introduced measurement gas within the chamber 16. Also, the measuring electrode 12 of the sensing cell is exposed to the atmosphere surrounding the inner pumping electrode 6, in the diffusion chamber 16.

On one side of the oxygen sensing cell on which the reference electrode 14 is formed, there are superposed a third and a fourth planar solid electrolyte body 22, 24 which cooperate with the second planar solid electrolyte body 10, to define an air passage 26 which is open to the ambient air at the longitudinal end of the sensing element 2 remote from the oxygen detecting portion. In this arrangement, the ambient air is introduced into the air passage 26 so that the reference electrode 14 of the sensing cell is exposed to the introduced air.

The stabilized zirconia used for the solid electrolyte bodies 4, 10, 22, 24 and the spacer layer 18, may be, for example, zirconium oxide doped with yttrium oxide or calcium oxide, as known in the art. The porous electrodes 6, 8, 12, 14 may be formed of platinum or similar metals.

A first multi-layered heater 28 is integrally formed on the surface of the fourth planar solid electrolyte body 24 remote from the air passage 26. A second multi-layered heater 30 is formed on the first planar solid electrolyte body 4, so as to surround the outer pumping electrode 8. In other words, these first and second heaters 28, 30, which are generally planar parallel to the plane of the solid electrolyte bodies 24, 4, are integrally formed so as to sandwich an assembly of the oxygen sensing and pumping cells, in order to heat these cells to an optimum operating temperature. Each of the first and second multi-layered heaters 28, 30 consists of a heat generating element 28a, 30a, an electrically insulating porous layer 28b, 30b substantially surrounding the heat generating element 28a, 30a, and a gas-tight layer 28c, 30c which cooperates with the adjacent solid electrolyte body 24, 4, to enclose the electrically insulating layer 28b, 30b and thereby isolate or protect the heat generating element 28a, 30a from the external measurement gas. The electrically insulating porous layers 28b, 30b are made of alumina or similar electrically resistive ceramic materials, while the gas-tight layers 28c, 30c are made of zirconia or similar solid electrolyte materials. The heat generating elements 28a, 30a are formed in a suitable manner, for example, by applying a film of cermet whose major component consists of a powdered mixture of alumina and platinum, for example.

The inner pumping electrode 6 and the measuring electrode 12 that are exposed to the atmosphere within the diffusion chamber 16 between the pumping and sensing cells, are covered by porous ceramic layers 32, 34, respectively. These ceramic layers 32, 34 are made of alumina or similar ceramic materials. Similarly, the outer pumping electrode 8 on the outer surface of the pumping cell is covered by a porous ceramic layer 26. Thus, the electrodes 6, 12, 8 are exposed to the internal or external measurement gas through the porous structures of these porous ceramic layers 32, 34, 36, respectively.

In the air passage 26 formed in the laminar structure of the sensing element 2, there is formed a thermosensitive layer 38 in the form of an annular ring so as to surround the reference electrode 14 of the sensing cell, with a suitable space left therebetween. The thermosensitive layer 38 consists of an electrically resistive thermosensitive element 38a, and an electrically insulating porous layer 38b in which the thermosensitive element 38a is embedded, so that the element 38a is electrically insulated from the adjacent solid electrolyte bodies 10, 22. For example, the electrically resistive thermosensitive element 38a consists of a thermistor made of a cermet having a high negative temperature coefficient of resistance, so that its electrical resistance decreases as the temperature increases. The cermet may be formed in a film which principally consists of a powdered mixture of a ceramic material such as zirconia or alumina, and platinum. If necessary, about 0.1–0.5% of $TiO_2$ may be added to the mixture.

The thus constructed integral laminar structure of the oxygen sensing element 2 is produced by co-firing superposed unfired layers of the constituent layers, that is, first heater 28, fourth and third solid electrolyte bodies 24, 22, oxygen sensing cell (10, 12, 14), thermosensitive layer 38, spacer layer 18, oxygen pumping cell (4, 6, 8) and second heater 30.

In the oxygen sensing element 2, the heat generating elements 28a, 30a of the first and second heaters 28, 30, and the thermosensitive element 38a of the thermosensitive layer 38, are connected at their one end to each other and to a common electric terminal "a". The other end of the heat generating elements 28a, 30a is connected to an electric terminal "c", while the other end of the thermosensitive element 38a is connected to an electric terminal "d". Further, the outer pumping electrode 8 of the pumping cell is connected to an electric terminal "b", while the inner pumping electrode 6 and the measuring electrode 12 of the sensing cell are connected to each other and to an electric terminal "e". The reference electrode 14 of the sensing cell is connected to an electric terminal "f". In summary, the terminals "a" and "c" are used as heater terminals, while the terminals "a" and "d" are used as temperature sensing terminals. The terminals "e" and "f" serve as voltage terminals, while the terminals "b" and "e" serve as limiting current terminals.

The electric terminals "a" through "f" indicated above are connected to appropriate devices, as shown in FIG. 1. Described in detail, the terminals "a", "c" and "d" are connected to a heater controller 40 which controls the amount of electric current to be applied to the first and second heaters 28, 30 (heat generating elements 28a, 30a), according to a temperature sensed by the thermosensitive layer 38 (thermosensitive element 38a) built in the sensing element 2, so that the oxygen sensing and pumping cells are heated by the heaters 28, 30 to a suitable operating temperature, thereby maintaining a uniform temperature distribution of the sensing element 2 as a whole.

An electromotive force is induced between the measuring and reference electrodes 12 and 14 of the oxygen sensing cell, based on a difference in oxygen concentration between the atmosphere within the diffusion chamber 16, and the atmosphere (air) within air passage 26, according to the principle of an oxygen concentration cell. The electromotive force applied to the terminal "f" is compared with a reference voltage of a reference voltage source 42, by a suitable comparator. The output of the comparator is applied to a pumping-current controller in the form of a PI controller 44. This controller is adapted to control a pumping current (Ip) to be applied to the oxygen pumping cell, by means of a voltage-current converter 46. More specifically, the PI controller applies a voltage signal to the voltage-current converter 46, so as to control the pumping current (Ip) so that the electromotive force to be induced by the oxygen sensing cell is equal to the reference voltage of the reference voltage source 42.

The voltage signal produced by the PI controller 44 is converted into a corresponding pumping current (Ip) by the voltage-current converter 46. The pumping current is applied via the electric terminals "b" and "e", between the outer and inner pumping electrodes 8, 6 of the pumping cell, to effect a controlled oxygen pumping action. More particularly, oxygen in the external measurement gas is pumped into the diffusion chamber 16 where the measurement gas is a reducing atmosphere, or alternatively the oxygen in the diffusion chamber 16 is pumped out where the measurement gas is an oxidizing atmosphere. This pumping action is controlled by the pumping current (Ip) so that the electromotive force induced by the sensing cell, which represents the atmosphere within the diffusion chamber 16, is equal to the reference voltage of the reference voltage source 42. That is, the atmosphere within the diffusion chamber 16, to be controlled by the oxygen pumping cell, is determined by the reference voltage.

The pumping current (Ip) to be applied to the oxygen pumping cell to effect an oxygen pumping action is changed depending upon a change in the measurement gas. The output voltage signal of the PI controller 44 that controls the pumping current (Ip) is also applied to an output converter 48, which in turn produces an output voltage signal (oxygen concentration signal) indicative of the positive or negative oxygen concentration of the measurement gas, depending upon whether the measurement gas is an oxidizing or reducing atmosphere. As described later in detail, both positive and negative oxygen concentration values are represented by positive output voltages (0 V to 1 V) produced by the output converter 48.

Described in greater detail, the direction of flow of the pumping current (Ip) applied to the pumping cell is reversed when the measurement gas to be introduced into the diffusion chamber 16 through the gas-inlet aperture 20 is changed from an oxidizing atmosphere to a reducing atmosphere, or vice versa. The output converter 48 stores data representative of a predetermined relationship between the pumping current Ip (+Ip or −Ip) or the voltage output from the PI controller 44, and the corresponding oxygen concentration signal (positive voltage level) which is varied to cover both the positive oxygen concentration range (where the measurement gas is an oxidizing atmosphere), and the negative oxygen concentration range (where the measurement gas is a reducing atmosphere). According to this stored relation, the output converter 48 converts the voltage signal (current control signal indicative of the pumping current Ip) from the PI controller 44, into the corresponding positive oxygen concentration voltage level which represents an oxygen concentration of the oxidizing measurement gas, or an amount of shortage or deficiency of oxygen of the reducing measurement gas (an additional amount of oxygen necessary to permit perfect combustion of an air-fuel mixture from which the measurement gas is produced).

As mentioned above, the pumping current (Ip) to be applied between the two pumping electrodes 6, 8 of the pumping cell is controlled by means of the PI controller 44 and the voltage-current converter 46, so that the oxygen concentration of the atmosphere within the diffusion chamber 16, more precisely, the oxygen concentration near the measuring electrode 12 exposed to the introduced measurement gas, is controlled to be maintained at a predetermined level (determined by the voltage of the reference voltage source 42). According to this control arrangment, the oxygen concentration $O_2(S)$ is obtained by the following equation (1):

$$O_2(S) = KIpO_2 \cdot IpO_2 - KIpH_2 \cdot IpH_2$$
$$- KIpCO \cdot IpCO + O_2(C) \quad (1)$$

where,
$KIpO_2$: Current coefficient of oxygen
$IpO_2$: Oxygen pumping current contributing to oxygen concentration
$KIpH_2$: Current coefficient of hydrogen
$IpH_2$: Oxygen pumping current necessary to consume hydrogen concentration
$KIpCO$: Current coefficient of carbon monoxide
$IpCO$: Oxygen pumping current necessary to consume carbon monoxide concentration
$O_2(C)$: Oxygen concentration within the diffusion chamber 16

The controlled oxygen pumping current (Ip) to be applied between the two pumping electrodes 6, 8 is obtained by the following equation (2):

$$Ip = IpO_2 - IpH_2 - IpCO \quad (2)$$

where,
$IpH_2 = IpCO = 0$ when the measurement gas is an oxidizing atmosphere, and
$IpO_2 = 0$ when the atmosphere gas is an reducing atmosphere.
According to the equation (2), therefore, $Ip = IpO_2$ is equal to or larger than zero where the oxidizing atmosphere is measured, and $Ip = -IpH_2 - IpCO$ is equal to or smaller than zero.

In order to detect both positive and negative oxygen concentrations of oxidizing and reducing atmospheres, the pumping current (Ip) is set at zero when the oxygen concentration of the atmosphere within the diffusion chamber 16 is zero. This atmosphere corresponds to a stoichiometric exhaust gas which is obtained as a result of combustion of an air-fuel mixture whose excess air ratio ($\mu$) is 1 (which has the stoichiometric air/fuel ratio). In this case, a circuit to calculate the oxygen concentration (positive or negative) based on the pumping current (Ip) is made relatively simple. However, it is possible that the pumping current is zero when the oxygen concentration $O_2(C)$ within the diffusion chamber 16 is at a given point above or below zero, which corresponds to the oxygen concentration (positive or negative) of an exhaust gas which is produced in combustion of an air-fuel mixture whose excess air ratio is higher or lower than one (1). In this case, the calculation of the oxygen concentration requires compensation for a biased value which corresponds to the oxygen concentration obtained when the pumping current is zero.

When the measurement gas is a reducing atmosphere, the well known water gas reaction ($H_2 + CO_2 \longleftrightarrow CO + H_2O$) takes place, and the condition in which $H_2$ and CO are produced differs depending upon the temperature, even if the excess air ratio (air/fuel ratio) of the air-fuel mixture corresponding to the reducing atmosphere is constant.

The water gas reaction occurs again within or near the diffusion chamber 16 of the sensing element 2, and the ratio of $H_2$ to CO is determined by the temperature within or in the vicinity of the diffusion chamber 2.

In view of the above, the negative oxygen concentration (amount of shortage of oxygen) of the reducing measurement gas, i.e., theoretical amount of oxygen necessary to permit perfect combustion of the air-fuel mixture is expressed by the following equation (3):

$$-O_2 = (H_2 - CO)/2 \quad (3)$$

Further, the negative oxygen concentration $O_2'$ is determined by the following equation (4), which is derived from the equation (1):

$$\begin{aligned} O_2' &= -KIpH_2 \cdot ipH_2 - KIpCO \cdot IpCO \\ &= KIp' \cdot Ip. \end{aligned} \quad (4)$$

Where $KIp'$ is constant, a linearity error $\epsilon$ between the negative oxygen concentration values obtained from the equations (3) and (4) is expressed by the following equation (5):

$$\epsilon = \frac{O_2' - (H_2 + CO)/2}{\text{Measuring Range}} \times 100\% \quad (5)$$

Figure 3:
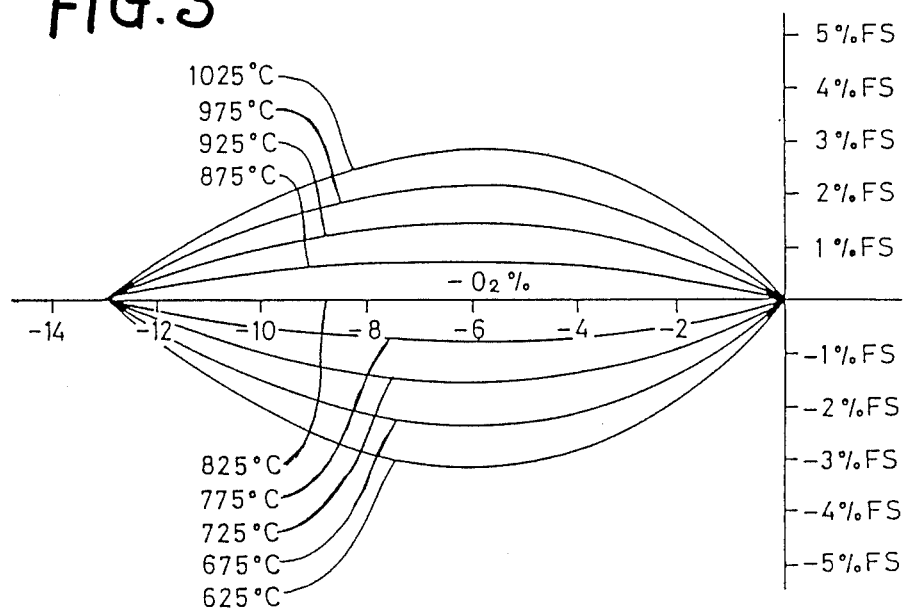
FIG. 3 is a graphical representation showing a relation between a linearity error and a temperature of the sensing element.

An experiment using simulation atmospheres (having known negative $O_2$ concentrations) revealed a relationship as shown in FIG. 3, among the linearity error $\epsilon$ calculated according to the equation (5), negative oxygen concentration $-O_2\%$, and temperature of the sensing element 2 (around the diffusion chamber 16). The measuring range of the negative oxygen concentration $-O_2\%$ is from 0 to $-13\%$, and the linearity error is expressed as full-scale (FS) percent. A relation between the maximum linearity error (positive and negative max.

Figure 4:
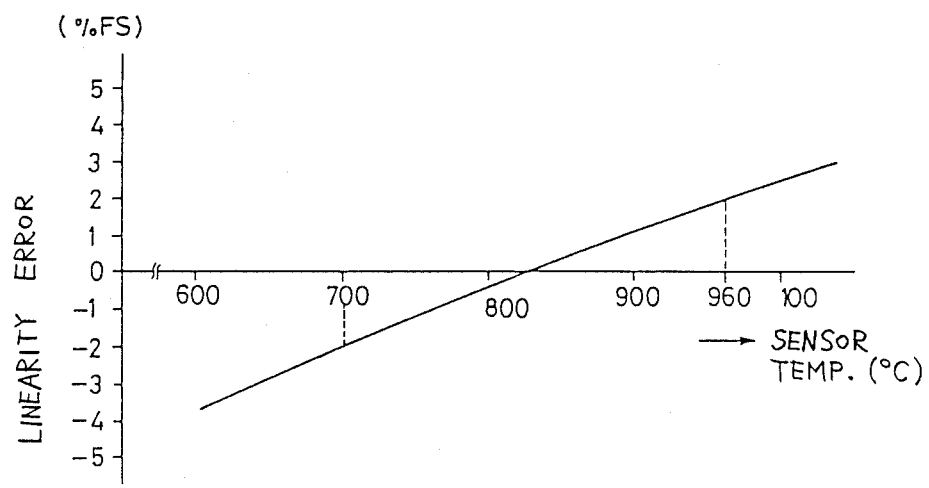
FIG. 4 is is a graph showing a relation between the maximum linearity error and the temperature of the sensing element.

%FS) and the sensor temperature (°C.) is shown in FIG. 4.

It will be understood from the graphs of FIGS. 3 and 4 that the sensor temperature, more precisely, the temperature of the oxygen sensing and pumping cells must be held within a range between 700° C. and 960° C., in order to assure a satisfactory sensing accuracy of the sensing element 2, i.e., within a range of plus 2.0%FS to minus 2.0%FS, where the measuring range of the negative oxygen concentration is 0 to −13%. The required temperature range differs depending upon the width of the measuring range. Within the above temperature range, the negative oxygen concentration can be obtained with a minimum linearity error, based on the pumping current (Ip) or the voltage output of the PI controller 44, according to the predetermined relation represented by a straight line "b" in FIG. 5.

Figure 5:
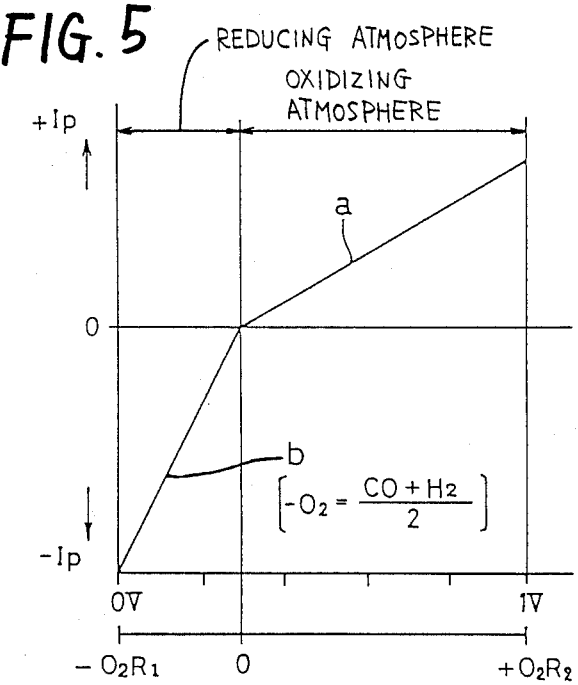
FIG. 5 is a graph showing a relation between an oxygen pumping current Ip and an output signal of the analyzing device indicative of positive and negative oxygen concentrations.

According to the invention, the linear relations represented by the straight lines "a" and "b" as indicated in FIG. 5 are predetermined based on simulation tests by using atmospheres which have known positive and negative oxygen concentrations. Described in more detail, the straight line "a" represents a relation between the positive pumping current +Ip (or output voltage of the PI controller 44), and the positive oxygen concentration $+O_2\%$ of the oxidizing atmosphere. This relation is obtained by using simulation atmospheres whose oxygen concentration values are known. The straight line "b", which represents the relation between the negative pumping current −Ip and the negative oxygen concentration $-O_2\%$, is obtained by using simulation atmospheres whose hydrogen and carbon monoxide concentration values are known. In this case, the equation $-O_2=(CO+H_2)/2$ is used to convert the total concentration of hydrogen and carbon monoxide into a negative oxygen concentration. The thus obtained relations "a" and "b" are stored in the output converter 48, which produces a voltage output based on the voltage output (which represents the pumping current Ip) received from the PI controller 44, and according to the stored relations. For instance, the voltage output to be produced by the output converter 48 ranges from 0 to 1V (FIG. 5), or 4 mA to 20 mA, so that this positive voltage range covers both the positive and the negative oxygen concentration ranges. In other words, both the oxidizing and the reducing atmospheres can be handled by the instant oxygen analyzing device, such that its output voltage level indicative of both positive and negative oxygen concentrations is varied only within a positive range as shown in FIG. 5 (or alternatively within a negative range), without being shifted across the zero level from the positive range to the negative range or vice versa.

The conversion of a positive or negative output of the PI controller 44 into a positive voltage output of the output converter 48, as indicated in FIG. 5, will assure a reduced amount of linearity error of the produced sensor output, relative to the corresponding positive and negative pumping current values Ip which correspond to the oxidizing and reducing measurement gases. In other words, the single output signal produced by the same output converter 48 represents an oxygen shortage amount of a reducing atmosphere, as well as an oxygen excess amount of an oxidizing atmosphere, with an increased level of measuring accuracy, even in the case where the measurement gas changes between oxidizing and reducing atmospheres, like an atmosphere within an industrial furnace. Thus, the instant oxygen analyzing device is particularly useful for handling such changing atmospheres.

While the present invention has been described in its preferred embodiment, it is to be understood that the invention is not limited to the precise details of the illustrated embodiment, but the invention may be embodied with various changes, modifications and improvements, which may occur to those skilled in the art, without departing from the spirit and scope of the invention.

Figure 6:
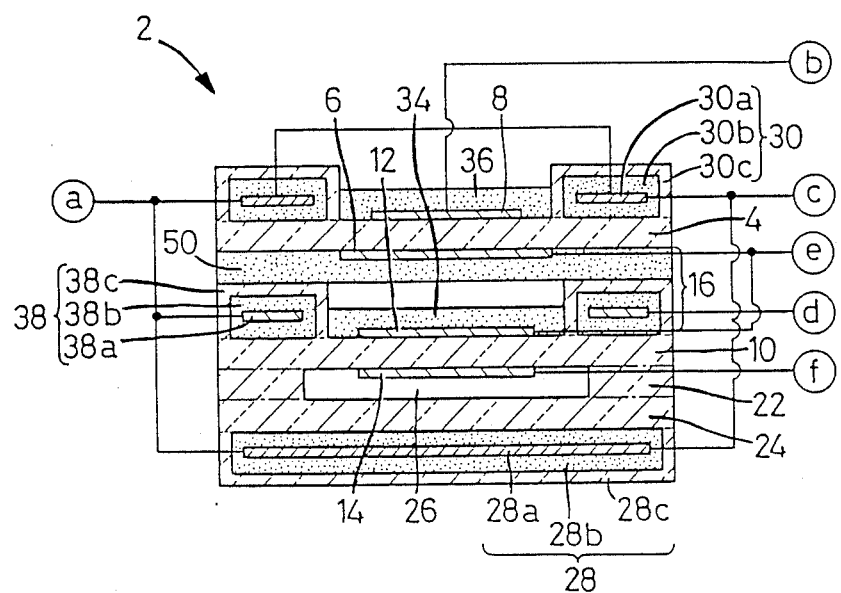
FIG. 6 is an elevational cross sectional view corresponding to that of FIG. 2, depicting a modified oxygen sensing element used in another embodiment of the invention.

For instance, the external measurement gas may be introduced into the diffusion chamber 16 through a porous ceramic layer 50, as illustrated in FIG. 6. In this case, the porous ceramic layer 50 is exposed at its lateral ends to the external measurement gas, and has a predetermined resistance to the molecules of the measurement gas. The inner pumping electrode 6 is exposed through the porous ceramic layer 50 to the atmosphere within the diffusion chamber 16. Similarly, the measuring electrode 12 is exposed to the atmosphere through the porous ceramic layer 34. Further, the thermosensitive layer 38 used in the present sensing element 2 of FIG. 6 is disposed within the diffusion chamber 16 between the sensing and pumping cells, such that the measuring electrode 12 of the sensing cell is surrounded by the thermosensitive layer 38. Unlike the thermosensitive layer 38 used in the preceding embodiment, the thermosensitive layer 38 shown in FIG. 6 includes a gas-tight layer 38 which covers the electrically insulating layer 38b and thereby isolates the electrically resistive thermosensitive element 38a from the external measurement gas.

It is also possible to provide means for raising the temperature of the measurement gas, preferably to a level substantially equal to the operating temperature of the sensing element, prior to effecting analysis of oxygen in the measurement gas, so that the water gas reaction of the measurement gas is stabilized before the sensing element produces an effective output signal.

What is claimed is:

1. An oxygen analyzing method for determining a positive or negative oxygen concentration of a measurement gas which changes at random between an oxidizing atmosphere and a reducing atmosphere, comprising the steps of:

providing an electrochemical oxygen sensing cell wherein an electromotive force is induced according to the principle of an oxygen concentration cell, between a measuring electrode exposed to said measurement gas, and a reference electrode exposed to a reference gas;

providing an electrochemical oxygen pumping cell adapted to effect an electrochemical oxygen pumping action for controlling an atmosphere adjacent to said measuring electrode of said sensing cell;

providing a heater which cooperates with said sensing and pumping cells to form an integral laminar oxygen sensing element, and which is energized to heat said sensing and pumping cells;

controlling said heater so as to maintain an operating temperature of said sensing and pumping cells within a range of 700°–960° C.;

producing a pump control signal for controlling a pumping current to be applied to said pumping cell, to control the atmosphere adjacent to said measuring electrode so that said electromotive force induced between said measuring and reference electrodes is equal to a predetermined level; and converting the controlling pumping current or the produced pump control signal, into an oxygen concentration signal whose level is held within one of a positive range and a negative range, said converting being performed according to a stored predetermined relationship between a value said pumping current or said pump control signal and said level of said oxygen concentration signal, said predetermined relationship consisting of a first relationship between a positive value of said pumping current or pump control signal and said positive or negative range of said level of the oxygen concentration signal, and a second relationship between a negative value of said pumping current or pump control signal and said positive or negative range of said level of the oxygen concentration signal, said second relationship being determined according to the equation $-O_2=(CO+H_2)/2$, wherein $-O_2$ represents the oxygen concentration of said measurement gas, and CO and $H_2$ represent known concentration values of a simulation atmosphere, said oxygen concentration signal representing said positive oxygen concentration of said measurement gas where the measurement gas is in a state of said oxidizing atmosphere, or said negative oxygen concentration of said measurement gas where the measurement gas is in a state of said reducing atmosphere.

2. An oxygen analyzing method according to claim 1, further comprising a step of providing a thermosensitive element incorporated in said oxygen sensing element, for sensing the operating temperature of said sensing and pumping cells, said step of controlling said heater being achieved based on said operating temperature sensed by said thermosensitive element.

3. An oxygen analyzing method according to claim 1, wherein said pumping current is controlled such that said predetermined level of the electromotive force corresponds to a stoichiometric atmosphere whose oxygen concentration is zero.

4. An oxygen analyzing method according to claim 1, wherein said oxygen concentration signal is a voltage signal whose level is positive.

5. An oxygen analyzing device for determining a positive or negative oxygen concentration of a measurement gas whcih changes at random between an oxidizing atmosphere and a reducing atmosphere, comprising:

an electrochemical oxygen sensing element including (a) an electrochemical oxygen sensing cell having a measuring electrode exposed to said measurement gas, and a reference electrode exposed to a reference gas, wherein an electromotive force is induced between said measuring and reference electrodes, according to the principle of an oxygen concentration cell, (b) an electrochemical oxygen pumping cell operable to effect an electrochemical oxygen pumping action for controlling an atmosphere adjacent to said measuring electrode of said sensing cell, (c) diffusion-resistance means through which said measurement gas diffuses toward said measuring electrode, under a predetermined diffusion resistance, and (d) a heater for heating said sensing and pumping cells;

a heater controller for controlling said heater so as to maintain an operating temperature of said sensing and pumping cells within a range of 700°–960° C.;

a pumping-current controller which produces a pump control signal for controlling a pumping current to be applied to said pumping cell, to control the atmosphere adjacent to said measuring electrode so that said electromotive force induced between said measuring and reference electrodes is equal to a predetermined level;

a converter for converting the controlled pumping current or the produced pump control signal, into an oxygen concentration signal whose level is held within one of a positive range and a negative range, said oxygen concentration signal representing said positive oxygen concentration of said measurement gas where the measurement gas is in a state of said oxidizing atmosphere, or said negative oxygen concentration of said measurement gas where the measurement gas is in a state of said reducing atmosphere; and said converter including means for storing a predetermined relationship between a value of said pumping current or said pump control signal and said level of said oxygen concentration signal, said predetermined relationship consisting of a first relationship between a positive value of said pumping current or pump control signal and said positive or negative range of said level of the oxygen concentration signal, and a second relationship between a negative value of said pumping current or pump control signal and said positive or negative range of said level of the oxygen concentration signal, said second relationship being determined according to the equation $-O_2=(CO+H_2)/2$, wherein $-O_2$ represents the oxygen concentration of said measurement gas, and CO and $H_2$ represent known concentration values of a simulation atmosphere.

6. An oxygen analyzing device according to claim 5, wherein said oxygen sensing element further comprises a thermosensitive element integrally incorporated therein for sensing said operating temperature of said sensing and pumping cells, said heater controller controlling said heater, based on said operating temperature sensed by said thermosensitive element.

7. An oxygen analyzing device according to claim 5, wherein said heater controller controls said heater so as to maintain said operating temperature within a range of 700°–960° C.

* * * * *